(12) United States Patent
Moreau

(10) Patent No.: US 9,277,798 B2
(45) Date of Patent: Mar. 8, 2016

(54) DISTRIBUTION AND APPLICATION HEAD

(71) Applicant: APTAR FRANCE SAS, Le Neubourg (FR)

(72) Inventor: Francis Moreau, Sotteville les Rouen (FR)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

(21) Appl. No.: 14/395,398

(22) PCT Filed: Apr. 16, 2013

(86) PCT No.: PCT/FR2013/050834
§ 371 (c)(1),
(2) Date: Oct. 17, 2014

(87) PCT Pub. No.: WO2013/156730
PCT Pub. Date: Oct. 24, 2013

(65) Prior Publication Data
US 2015/0086259 A1    Mar. 26, 2015

(30) Foreign Application Priority Data

Apr. 20, 2012  (FR) ...................................... 12 53630

(51) Int. Cl.
  *A45D 34/04* (2006.01)
  *B05B 11/00* (2006.01)
  *A61M 35/00* (2006.01)
  *B65D 83/28* (2006.01)
  *B65D 83/30* (2006.01)

(52) U.S. Cl.
  CPC .............. *A45D 34/04* (2013.01); *A61M 35/003* (2013.01); *B05B 11/0091* (2013.01); *B05B 11/3032* (2013.01); *A45D 2200/056* (2013.01); *A45D 2200/155* (2013.01); *B05B 11/0048* (2013.01); *B65D 83/285* (2013.01); *B65D 83/30* (2013.01)

(58) Field of Classification Search
  CPC .................... A45D 2200/15; A45D 2200/155; A45D 2200/157
  USPC ........................................ 401/1, 2, 261–267
  See application file for complete search history.

(56) References Cited

U.S. PATENT DOCUMENTS

2003/0063945 A1    4/2003   Gueret

FOREIGN PATENT DOCUMENTS

| EP | 1 293 448 A2 | 3/2003 |
|----|--------------|--------|
| FR | 2 954 936 A1 | 7/2011 |
| WO | 2010/141159 A2 | 12/2010 |

OTHER PUBLICATIONS

International Search Report for PCT/FR2013/050834 dated Aug. 7, 2013.
International Preliminary Report on Patentability, issued by the International Searching Authority in corresponding Application No. PCT/FR2013/050834.

*Primary Examiner* — David Walczak
*Assistant Examiner* — Joshua Wiljanen
(74) *Attorney, Agent, or Firm* — Sughrue Mion, PLLC

(57) ABSTRACT

A dispenser and applicator head for associating with a dispenser unit, such as a pump, a valve, or a squeezable tube, the head including an applicator pad defining an outer applicator face for coming into contact with the skin, the pad being made essentially of a heat-transfer material so as to impart a cold sensation on contact with the skin, the pad defining a thickness from an inner face to the outer face, the pad having a dispenser passage passing through it, which passage puts the inner face into communication with the outer face. The applicator pad presents a small thickness at the dispenser passage.

9 Claims, 2 Drawing Sheets

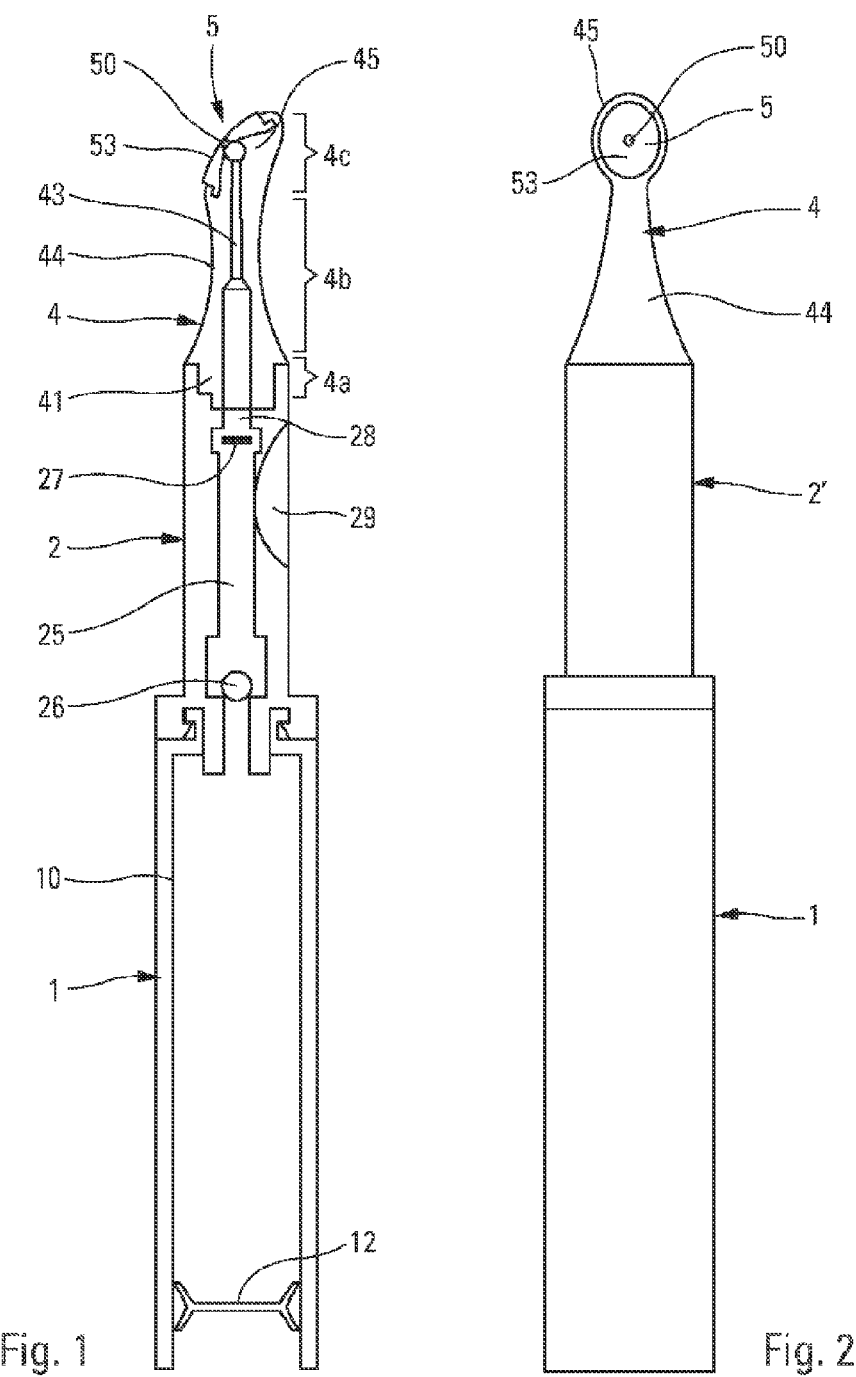

DISTRIBUTION AND APPLICATION HEAD

CROSS REFERENCE TO RELATED APPLICATIONS

This application is a National Stage of International Application No. PCT/FR2013/050834 filed Apr. 16, 2013, claiming priority based on French Patent Application No. 12 53630 filed Apr. 20, 2012, the contents of all of which are incorporated herein by reference in their entirety.

The present invention relates to a dispenser and applicator head for associating with a dispenser unit, such as a pump, a valve, a squeezable tube, etc. The head includes an applicator pad defining an outer applicator face for coming into contact with the skin, the pad being made essentially of a heat-transfer material so as to impart a cold sensation on contact with the skin, the pad defining a thickness from an inner face to the outer face, the pad having a dispenser passage passing through it, which passage puts the inner face into communication with the outer face. Advantageous fields of application of the present invention are the fields of cosmetics, perfumery, and pharmacy.

In the fields of cosmetics and pharmacy, fluid dispensers already exist comprising a fluid reservoir associated with a rigid and heat-transfer dispenser head for putting into contact with the skin, in particular the skin of the face. Documents WO 2010/141158, WO 2010/141159, and FR 2 915 972 are known, for example. The head forms an applicator pad from which a dispenser orifice opens out. The user actuates the dispenser so as to dispense a dose of fluid, and then spreads it by means of the applicator pad which provides a massaging effect and above all a cold sensation on contact with the skin which is very pleasant.

In document FR 2 915 972, the pad that is made of metal or ceramic defines a borehole in which a plastics insert is received that forms an outlet duct and the dispenser orifice. As a result, the fluid that is dispensed is never in contact with the borehole, but the orifice is visibly formed by a part (the insert) that is distinct from the pad, which is not particularly attractive.

In documents WO 2010/141158 and WO 2010/141159, the pad includes a frustoconical dispenser passage defining, on its inner face, a very wide inlet, and on its outer face, a dispenser orifice. The fluid that is dispensed comes into contact with the entire frustoconical passage and cools on contact therewith. It can also be said that the fluid heats the pad as a result of extended contact. In the present invention, the fluid comes into contact with the dispenser passage, as in the above-mentioned documents WO 2010/141158 and WO 2010/141159.

The present invention seeks to preserve the advantages of the prior-art pads, while eliminating their drawbacks. The fluid should pass directly through the pad (without insert), but without thereby heating it. Another object of the present invention is to facilitate possible treatment of the surface of the pad, in particular at the dispenser passage.

To do this, the present invention proposes a dispenser and applicator head for associating with a dispenser unit, such as a pump, a valve, or a squeezable tube, the head including an applicator pad defining an outer applicator face for coming into contact with the skin, the pad being made essentially of a heat-transfer material so as to impart a cold sensation on contact with the skin, the pad defining a thickness from an inner face to the outer face, the pad having a dispenser passage passing through it, which passage puts the inner face into communication with the outer face, the applicator pad being made of metal, such as zamak, and being covered with a coating made of inert material, such as nickel and/or chromium, at least at the dispenser passage and the applicator surface, the head further including a body made of plastics material, said body defining a connection section for connecting to the dispenser unit, an application section in engagement with the inner face of the applicator pad, and an interconnection section connecting the connection section to the application section, the body defining a dispenser channel that communicates with the dispenser passage beside the inner face, the applicator pad presenting a minimum thickness at the passage lying in the range about 1 millimeter (mm) to 4 mm.

Thus, the fluid passes directly through the pad by passing through the dispenser passage, and is heated little because the dispenser passage is very short. For the user, the fluid is dispensed directly from the pad (and not from a plastic insert), and the pad remains "cold" since it is influenced very little by the fluid.

By way of example, the inner face may present concavity that is greater than the convexity of the outer face.

The shallow depth of the dispenser passage makes it possible to apply a coating to the pad without risk of imperfection at the passage. Specifically, if the passage were long and narrow, it would be extremely difficult to guarantee good application of the coating in the passage. In particular, such a coating is necessary with a pad made of zamak, which is not inert for certain fluids, such as cosmetic creams: it is thus necessary to apply an inert protective or barrier coating thereto.

Advantageously, the interconnection section is flexible, such that the applicator pad is movable relative to the connection section. Advantageously, the application section is overmolded on the applicator pad.

According to another characteristic, the application section is in contact with the major fraction of the inner face of the applicator pad. Advantageously, the dispenser channel includes a downstream end that is directly adjacent to the dispenser passage. Preferably, the dispenser channel defines a cavity that is substantially spherical, immediately upstream from the dispenser passage.

One of the principles of the present invention resides in forming a dispenser passage through the pad that is very short, the fluid being fed directly into the passage, preferably without any prior contact with the pad. Such a pad may easily be coated with an inert layer, if necessary.

In the figures:

FIG. 1 is a vertical-section view through a fluid dispenser in an embodiment of the invention;

FIG. 2 is an elevation view of the FIG. 1a dispenser;

Figure 3:
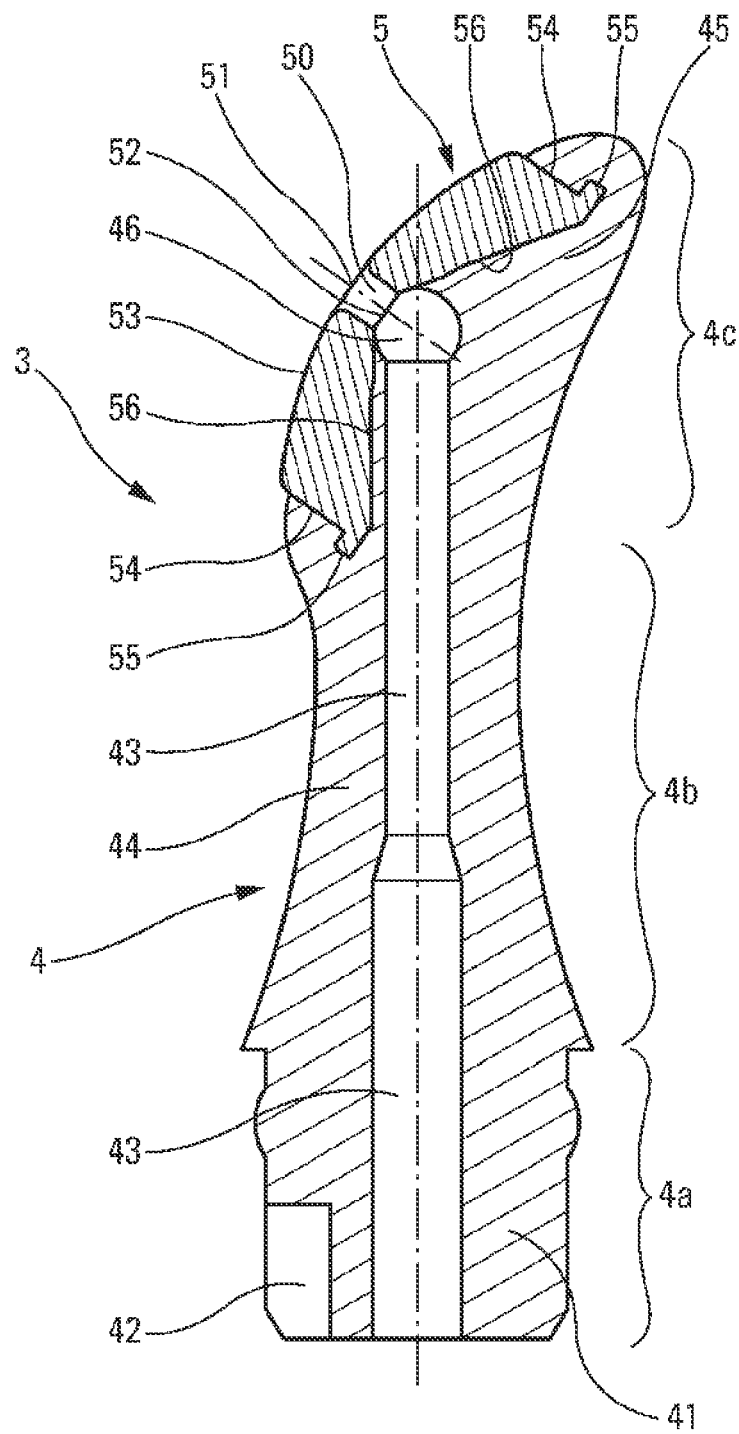
FIG. 3 is a larger-scale vertical section view through the dispenser head in FIGS. 1 and 2.

Reference is made initially to FIGS. 1 and 2 in order to describe in detail the structure of the fluid dispenser in the first embodiment of the invention. The dispenser essentially comprises five component elements, namely a fluid reservoir 1, a dispenser unit 2 that is a laterally-actuated pump in this embodiment, and a dispenser head 3 that is constituted by a connection and interconnection piece 4 associated with an applicator pad 5.

The fluid reservoir 1 may be of any kind, of any shape, and made of various appropriate materials. In the field of cosmetics, it is common to use a particular reservoir, as shown in FIG. 1, that comprises a cylindrical slide cylinder 10 associated with a follower piston 12 that moves along the cylinder 10 as fluid is removed therefrom. This type of reservoir makes it possible to keep the fluid out of contact with the outside air. When the reservoir is full, the follower piston 12 is located at an end of the cylinder 10 that is remote from the other end of the cylinder where a neck 11 is formed that defines an opening that puts the inside of the reservoir into communication with the outside. This design is entirely conventional for a reservoir of the follower-piston type.

The pump 2 is a laterally-actuated pump 2 that is mounted on the reservoir 1. The pump 2 includes an inlet valve 26 and an outlet valve 27 between which there is formed a pump chamber 25 including a laterally-actuated wall 29 that makes it possible to reduce the internal volume of the chamber 25. It should be observed that the outlet 28 of the pump 2 is stationary and situated on the axis of the pump and of the dispenser. The head 3 is mounted on the outlet 28 of the pump 2 such that it is not subjected to any movement while the pump 2 is being actuated by the lateral pusher 29.

The dispenser and applicator head 3 is mounted on the outlet 28 of the pump 2 and includes an internal delivery duct 43 that connects the outlet 28 to a dispenser passage 50. As already mentioned, the dispenser and applicator head 3 is constituted by a connection and interconnection piece 4 associated with an applicator pad 5. The connection and interconnection piece 4 is made of plastics material, whereas the applicator pad 5 is made of a rigid or hard heat-transfer material, such as metal, ceramic, an inorganic material, etc. that is suitable for imparting a cold sensation on contact with the skin. Preferably, the pad 5 is made of zamak coated with an inert protective barrier layer, such as nickel and/or chromium.

With reference to FIG. 3, there can be seen the detailed structure of the dispenser and applicator head 3. The applicator pad 5 is a solid single piece that is preferably circularly symmetrical. It defines an outer applicator face 53 and an inner face 56 that is in intimate contact with the connection and interconnection piece 4. On its outer periphery, the pad 5 defines an annular edge face 54 that may be formed with a projecting fastener bead 55. The bead 55 may be adjacent to the inner face 56. The pad 5 has a dispenser passage 50 passing therethrough that interconnects the two faces 53, 56. On the outer face 53, the dispenser passage 50 defines a dispenser orifice 51, and on the inner face 56, the dispenser passage 50 defines an inlet orifice 52. The dispenser passage 50 is advantageously situated at the center of the pad 5, but an off-center arrangement can also be envisaged. The dispenser passage 50 defines a dispensing axis that extends obliquely upwards relative to the longitudinal axis of the head 3.

The outer applicator face 53 is convex or bulging: its function is to receive a dose of fluid and to spread it or to apply it on an application surface, such as the skin of the face. The inner face 56 is concave, e.g. of generally dished shape. It should be observed that the concavity of the inner face is greater than the convexity of the outer face 53, such that the thickness of the pad is greater at its outer periphery than at its center where the dispenser passage 50 is advantageously situated. In other words, the pad 5 presents a minimum thickness around the dispenser passage 50. It can thus be said that the dispenser passage 50 is shallow or short, e.g. its length lies in the range about 1 mm to 4 mm. Its diameter may also be in the range about 1 mm to 4 mm, such that its diameter/depth ratio may be about 1, as is approximately the situation in FIG. 3. With a dispenser passage 50 having such a configuration, it is easy to apply an inert coating to the wall of the passage, which would not be possible with a passage that is long or deep.

As mentioned above, the applicator pad 5 is associated, preferably by overmolding, with the connection and interconnection piece 4 so that together they form the dispenser and applicator head 3. The connection and interconnection piece 4 defines three distinct sections, namely a connection section 4a, an interconnection section 4b, and an application section 4c together with the applicator pad 5. More precisely, the plastics material constituting the piece 4 is overmolded on the applicator pad 5 in such a manner as to form a kind of overmolded shell 45. The overmolded shell 45 extends around the edge face 54 and the bead 55, and over almost all of the surface of the inner face 56. It should be observed that directly upstream from the dispenser passage 50, i.e. upstream from the inlet orifice 52, the section 4c forms a cavity 46 that is partially or substantially spherical, having a diameter that is greater than the diameter of the dispenser passage 50. The cavity 46 is wide open to the dispenser passage 50 via the inlet orifice 52, and comes into annular contact with the portion of the inner face 56 that borders the inlet orifice 52. The cavity 46 is extended upstream by a dispenser channel 43 that extends through the other two sections 4b and 4a. While the piece 4 is being overmolded on the pad 5, the channel 43 and the cavity 46 are formed by an elongate molding pin which, at its free end, includes a spherical ball that corresponds to the cavity. As a result of its spherical shape, the ball may easily and reliably come into annular leaktight intimate contact with the edge of the inlet orifice 52 of the pad 5. During unmolding, the pin is removed from the piece 4 with force, in particular when the ball presents a diameter that is greater than the diameter of the channel, as in FIG. 3.

The interconnection section 4b, that is connected upstream from the application section 4c, forms a connection tube 44 that internally defines the dispenser channel 43. Advantageously, in the interconnection tube 43, the interconnection section 4b is elastically deformable. Such deformability is imparted by the intrinsic qualities of the plastics materials used and/or by having small wall thicknesses at this location. At its bottom end, the interconnection section 4b is extended by the connection section 4a that comprises a connection sleeve 41 that is engaged with the outlet 28 of the pump. The sleeve 41 may incorporate an orientation profile 42 that cooperates with a complementary profile of the pump so as to determine the angle of the head 3 relative to the pump 2. The connection section 4a presents stiffness that is greater than the stiffness of the interconnection section 4b, mainly as a result of the increased wall thicknesses.

The dispenser and applicator head 3 associates a heat-transfer and cold sensation applicator pad with a connection and interconnection piece 4. Once in place on the pump 2, the user may press on the pusher 29 so as to dispense a dose of fluid at the dispenser orifice 51. Then, the pad may be applied to a desired application surface, such as the skin, and the fluid may be spread by moving the pad over the skin, thereby imparting a cold massage sensation thereto. The movements of the hand imparted to the reservoir 1 are transmitted to the pad with an attenuated or damped effect, as a result of the springiness of the interconnection section 4b.

Without going beyond the ambit of the invention, the pad 5 could be asymmetric, the dispenser passage 50 could be off-center, the dispenser passage 50 could extend along the axis of the dispenser channel 43 or perpendicularly thereto, the shell 45 could extend over a portion only of the inner face 56, the shell 45 need not extend over the edge face 54, the head 3 could be mounted at the outlet of a conventional axially-actuated pump, of a valve, or of a squeezable tube.

The shallow depth of the dispenser passage 50 makes it possible for the fluid to pass directly through the pad, but without disturbing it thermally. Furthermore, when the pad is made of a material that is not inert, such as zamak, it is possible to apply an inert coating even at the dispenser passage 50 as a result of its shallow depth.

The invention claimed is:

1. A dispenser and applicator head for associating with a dispenser unit, such as a pump, a valve, or a squeezable tube, the head including an applicator pad defining an outer applicator face for coming into contact with the skin, the pad being made essentially of a heat-transfer material so as to impart a cold sensation on contact with the skin, the pad defining a thickness from an inner face to the outer face, the pad having a dispenser passage passing through it, which passage puts the inner face into communication with the outer face, the applicator pad being made of zamak, and being covered with a protective barrier layer made of inert material, at least at the dispenser passage and the application surface, the head further including a body made of plastics material, said body defining a connection section for connecting to the dispenser unit, an application section in engagement with the inner face of the applicator pad, and an interconnection section connecting the connection section to the application section, the body defining a dispenser channel that communicates with the dispenser passage beside the inner face;

the head being characterized in that the applicator pad presents a minimum thickness at the dispenser passage, said thickness lying in the range about 1 mm to 4 mm.

2. A head according to claim 1, wherein the applicator pad includes a peripheral zone of greater thickness and a central zone of smaller thickness, the dispenser passage being formed through the zone of smaller thickness.

3. A head according to claim 1, wherein the inner face presents concavity that is greater than the convexity of the outer face.

4. A head according to claim 1, wherein the interconnection section is flexible, such that the applicator pad is movable relative to the connection section.

5. A head according to claim 1, wherein the application section is overmolded on the applicator pad.

6. A head according to claim 1, wherein the application section is in contact with the major fraction of the inner face of the applicator pad.

7. A head according to claim 1, wherein the dispenser channel includes a downstream end that is directly adjacent to the dispenser passage.

8. A head according to claim 1, wherein the dispenser channel defines a cavity that is substantially spherical, immediately upstream from the dispenser passage.

9. A head according to claim 1, wherein the protective barrier layer is made of nickel and/or chromium.

* * * * *